May 16, 1972 O. F. SPRING Plant Pat. 3,169
CRAPE MYRTLE
Filed May 20, 1970
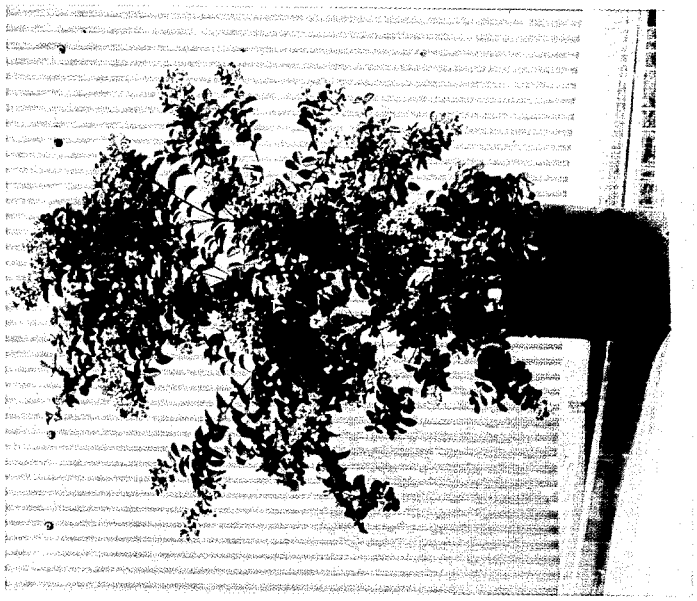
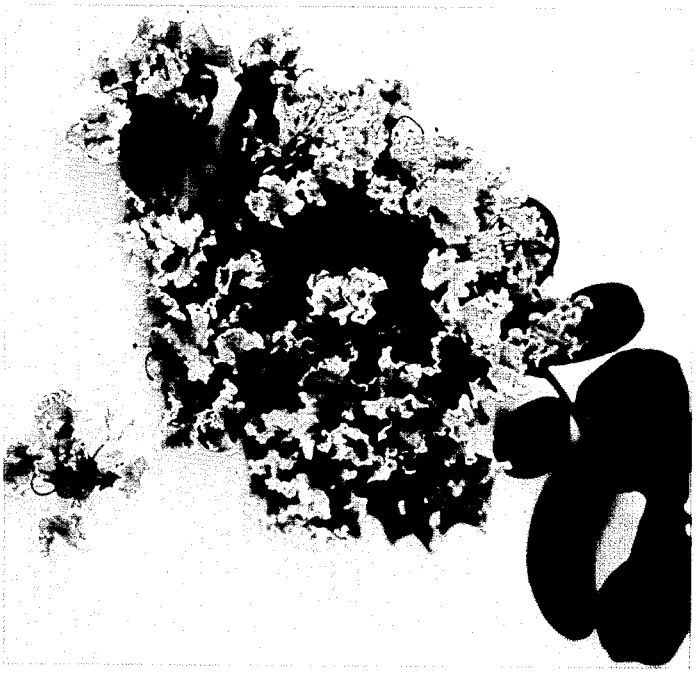
INVENTOR.
OTTO F. SPRING,
By Edmond F. Shanahan
ATTORNEY.

United States Patent Office

Plant Pat. 3,169
Patented May 16, 1972

3,169
CRAPE MYRTLE

Otto F. Spring, Okmulgee, Okla., assignor to Monrovia Nursery Company, Azusa, Calif.

Filed May 20, 1970, Ser. No. 39,184
Int. Cl. A01h 5/00
U.S. Cl. Plt.—54 1 Claim

ABSTRACT OF THE DISCLOSURE

A new and distinct variety of the Lagerstroemia genus characterized as to novelty by its compact, upright habit of growth and by flower clusters recognizably different from other Lagerstroemia, particularly by the red petals with white borders creating a picotee effect.

The present discovery relates to a new and distinct variety of ornamental shrub of the genus *Lagerstroemia indica,* commonly known as crape myrtle, characterized as to novelty by its compact, upright habit of growth and its unusual flowers, described in the following paragraphs and illustrated in the accompanying color drawing.

The new variety was discovered by me in the year 1966, growing as a chance seedling among many plants which I was breeding in an effort to produce a new ornamental plant. It is so distinct in shape of shrub and appearance of flower that no other variety of *Lagerstroemia indica,* known to me, can be specified as bearing similarity to the plant of the present patent application.

The plant has been asexually reproduced by me by means of cuttings. Cuttings have been taken from the original plant and all subsequent propagation has been from the plants grown from these cuttings. All descendants have shown the same characteristics as the original plant, indicating that the new variety is thereby well established. The plant does not produce true from seed.

The new variety does not resemble its seed parent, but has a more upright growth and distinctively different flowers.

The plant of the new variety, and a branch with flowers cut therefrom, are shown in full color in the accompanying illustration.

A detailed description of the new variety follows, and to facilitate identification of the important colors, the color terminology adopted by the British Horticultural Colour Charts has been followed.

The plant

Parentage: The pollen and seed parents of this plant were unnumbered or un-named seedlings that had shown desirable characteristics of growth and floor color, resulting from previous crosses made by me.

Growth: The plant is comparatively compact, upright and slightly spreading in its habit of growth. The ultimate height and width of the plant is not known, but it is thought to be somewhat taller in height than width in spread.

Branches: The plant is loosely branched from just above the ground level with the main branches ascending and the branchlets arching. The plant does not develop a central leader or trunk. New growth is light green, rapidly changing to light brown and later to a darker brown as the branches mature.

Foliage:

The leaves are of good substance and are semi-glossy.

*Shape.*—The leaves are best described as being opposite and broadly elliptic, with entire margins. The apex of the leaf is mucronulate and the base is obtuse. The leaves have very short petioles and the blades are from 1 inch to 1¾ inches in length and ⅝ inch to 1¼ inches in width. The midrib is slightly recessed on the upper side and is very prominent beneath, appearing light green in color.

*Color.*—The upper side of the leaf is best described as being Parsley Green 00962/1, while the lower side is Spinach Green 0960/2.

Flower:

The flower clusters appear as terminal panicles. The flowers are bisexual, 1¼ inches to 1½ inches across, regular, and pediceled. Color.—The basic color of the petals is Spiraea Red 025/1, and each petal has a narrow border of white, creating a picotee effect.

I claim:

1. A new and distinct variety of *Lagerstroemia indica* plant substantially as shown and described, characterized by its compact growth and unusual white-bordered, red-colored flower petals.

No references cited.

ROBERT. E. BAGWILL, Primary Examiner